United States Patent [19]

Tanaka et al.

[11] Patent Number: 5,091,563
[45] Date of Patent: Feb. 25, 1992

[54] PROCESS FOR PREPARING α-PHENYLPROPIONIC ACID DERIVATIVE

[75] Inventors: Yasutaka Tanaka; Hidetaka Kojima; Yasuo Tsuji, all of Himeji, Japan

[73] Assignee: Daicel Chemical Industries, Ltd., Osaka, Japan

[21] Appl. No.: 453,154

[22] Filed: Dec. 11, 1989

Related U.S. Application Data

[63] Continuation of Ser. No. 315,525, Feb. 24, 1989, abandoned, which is a continuation of Ser. No. 103,309, Sept. 30, 1987, Pat. No. 4,843,172.

[30] Foreign Application Priority Data

Dec. 24, 1986 [JP] Japan ............... 61-313868

[51] Int. Cl.$^5$ ............................................. C07C 51/10
[52] U.S. Cl. .................................................... 562/406
[58] Field of Search ............................... 562/406, 519

[56] References Cited

U.S. PATENT DOCUMENTS

| | | | |
|---|---|---|---|
| 2,805,248 | 9/1957 | Friederich | 562/519 |
| 3,689,533 | 9/1972 | Schultz | 562/406 |
| 3,813,428 | 4/1974 | Paulik | 562/519 |
| 4,659,518 | 4/1987 | Rizikalla | 562/519 |

FOREIGN PATENT DOCUMENTS 144935  6/1985  European Pat. Off. ............ 562/519

*Primary Examiner*—Michael L. Shippen
*Attorney, Agent, or Firm*—Flynn, Thiel, Boutell & Tanis

[57] ABSTRACT

A process for preparing an α-phenylpropionic acid derivative wherein an α-phenylethyl alcohol derivative is reacted with carbon monoxide in the presence of a catalyst to give an α-phenylpropionic acid derivative, which comprises carrying out the reaction in either one of the following manners (I), (II) and (III):

(I) effecting said reaction in the presence of a rhodium catalyst, as said catalyst, together with an iodine compound in such an amount as to give a Rh to I ratio on an atomic basis of 1:0.5 to 1:6; adjusting the concentration of water in the reaction mixture to a level of 2 mol/l or below; and employing a reaction temperature of 130° C. or below, (II) employing a mixture of a hydrocarbon and an oxygen-containing organic compound as a solvent, or (III) effecting said reaction in the presence of a rhodium catalyst, as said catalyst, and an iodine compound; adding water optionally together with an oxygen-containing organic compound as an extraction solvent to the resulting reaction mixture to thereby separate the same into two layers, i.e., a layer containing the reaction product and an aqueous layer; and repeatedly using the rhodium catalyst contained in said aqueous layer.

7 Claims, No Drawings

PROCESS FOR PREPARING α-PHENYLPROPIONIC ACID DERIVATIVE

This application is a continuation of U.S. Ser. No. 07/315 525, filed Feb. 24, 1989, now abandoned, which is a continuation of Ser. No. 07/103,309, filed Sept. 30, 1987, now U.S. Pat. No. 4,843,172.

BACKGROUND OF THE INVENTION

This invention relates to a process for preparing α-phenylpropionic acid on an industrial scale.

α-Phenylpropionic acid, which exhibits various pharmacological effects including analgesic, anti-inflammatory and antipyretic ones, is useful as a medicine.

Recently there have been proposed a number of pathways for synthesizing α-phenylpropionic acid. For example, there have been attempted some processes for preparing α-phenylpropionic acid in a single step by reacting an α-phenylethyl alcohol derivative or a styrene derivative with carbon monoxide.

Japanese Patent Laid-Open No. 10545/1984 discloses a process for preparing α-phenylpropionic acid from a styrene derivative with the use of a palladium complex as a catalyst. In spite of the high yield, this process is inferior to a process wherein an α-phenylethyl alcohol derivative is directly carbonylated, since the styrene derivative should be prepared through dehydration of an α-phenylethyl alcohol derivative wherein the high polymerization activity of the styrene derivative results in a poor dehydration yield.

Regarding the direct carbonylation of an α-phenylethyl alcohol derivative, it is known that a palladium complex catalyst is effective in carbonylating α-(alkoxyphenyl)ethyl alcohol but is useless for other α-phenylethyl alcohol derivatives (cf. Japanese Patent Laid-Open No. 95238/1984). Further there has been reported a process for carbonylating an α-phenylethyl alcohol derivative with the use of a cobalt or rhodium complex in the presence of water (cf. Japanese Patent Laid-Open No. 97930/1977). However this process seems hardly effective, since no α-phenylpropionic acid was prepared in our follow-up examination thereof (cf. Comparative Example 1).

On the other hand, there is known a process for preparing a carboxylic acid not from an α-phenylethyl alcohol derivative but from a common alcohol with the use of rhodium and an iodine compound as catalysts (cf. Japanese Patent Publication No. 3334/1972). When this process is applied to a process for preparing α-phenylpropionic acid from an α-phenylethyl alcohol derivative, which is to be carried out at such a high concentration of the iodine compound and a high reaction temperature as will be described in Examples hereinafter, however, the extremely high polymerization activity of said derivative results in the formation of a large amount of a polymer as a by-product and thus the desired α-phenylpropionic acid can be hardly obtained (cf. Comparative Example 2).

DISCLOSURE OF THE INVENTION

The present invention provides a process for preparing an α-phenylpropionic acid derivative wherein an α-phenylethyl alcohol derivative of the general formula:

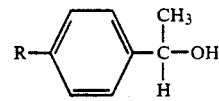

wherein R represents a hydrogen atom or an alkyl, alkenyl or aryl group, is reacted with carbon monoxide in the presence of a catalyst to form an α-phenylpropionic acid derivative of the general formula:

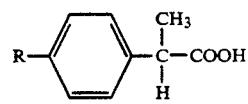

wherein R is as defined above,
which comprises carrying out the reaction in either one of the following manners (I), (II) and (III):
(I) effecting said reaction in the presence of a rhodium catalyst, as said catalyst, together with an iodine compound in such an amount as to give a Rh to I ratio on an atomic basis of 1:0.5 to 1:6; adjusting the concentration of water in the reaction mixture to a level of 2 mol/l or below; and employing a reaction temperature of 130° C. or below,
(II) employing a mixture of a hydrocarbon and an oxygen-containing organic compound as a solvent, or
(III) effecting said reaction in the presence of a rhodium catalyst, as said catalyst, and an iodine compound; adding water optionally together with an oxygen-containing organic compound as an extraction solvent to the resulting reaction mixture to thereby separate the same into two layers, i.e., a layer containing the reaction product and an aqueous layer; and repeatedly using the rhodium catalyst contained in said aqueous layer.

Now the present invention will be described with regard to each of the above manners (I), (II) and (III).

(I) It has been found that α-phenylpropionic acid can be prepared at a high yield by effecting the reaction of the present invention with the use of rhodium as a catalyst together with an iodine compound in such an amount as to give a Rh to I ratio on an atomic basis of 1:0.5 to 1:6; adjusting the concentration of water to a level of 2 mol/l or below; and employing a reaction temperature of 130° C. or below. Thus there has been established a process for advantageously preparing α-phenylpropionic acid on an industrial scale from an α-phenylethyl alcohol derivative and carbon monoxide in a single step, thus completing the present invention.

Now the reaction conditions will be described in detail.

(1) Catalyst

Rhodium compounds commonly used as the rhodium catalyst include rhodium halides, rhodium carbonyls and rhodium acetate. The rhodium catalyst may be fed together with the starting materials in initiating the reaction. Alternately, it may be converted into a carbonyl complex under pressurizing with carbon monoxide and hydrogen at a temperature of 100° to 200° C. prior to the initiation of the reaction.

When rhodium iodide is to be used as the catalyst, it is preferable to subject the same to a pretreatment for solubilization.

(2) Iodine compound

It is necessary to add an iodine compound such as $I_2$, HI or alkyl iodides to the reaction mixture as a cocatalyst in such an amount as to give a ratio of Rh to I on an atomic basis of 1:0.5 to 1:6. When rhodium iodide is to be used as the rhodium catalyst, it is not always necessary to further add an iodine compound.

(3) Starting alcohol

The alcohol to be used as a starting material is an α-phenylethyl alcohol derivative of the following general formula:

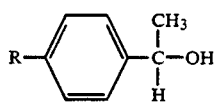

wherein R represents a hydrogen atom or an alkyl, alkenyl or aryl group. It is preferable that R represents a hydrogen atom, an alkyl or alkenyl group having one to six carbon atoms or a cycloalkyl group having three to six carbon atoms. Alternately R may represent a phenyl group optionally substituted by alkyl group(s) each having one to three carbon atoms or a naphthyl group. In particular, examples of R include straight-chain, branched or cyclic alkyl or alkenyl groups such as methyl, ethyl, propyl, isobutyl, isoprenyl and cyclohexyl groups; and aryl groups such as phenyl, tolyl, xylyl and naphthyl groups.

(4) Carbon monoxide

Pure carbon monoxide may be employed. Alternately, a mixture thereof with an inert gas such as nitrogen or hydrogen may be used. The reaction would proceed either under atmospheric or elevated pressure. By taking into consideration the reaction rate and cost, it is preferable to effect the reaction under atmospheric pressure to 100 kg/cm$^2$. When a mixture of carbon monoxide and hydrogen is to be used, a partial pressure of the latter of atmospheric pressure to 5 kg/cm$^2$ is rather preferable for accelerating the dissolution of the rhodium compound. A partial pressure thereof exceeding the above range is disadvantageous since the formation of a hydrogenated compound as a by-product may be accelerated thereby.

(5) Reaction temperature

The reaction may be usually effected at a temperature of 130° C. or below, preferably 30° to 130° C. A particularly preferable reaction temperature ranges from 60° to 100° C. from the viewpoints of suppressing the formation of by-products and economically effecting the reaction.

(6) Solvent

Although the reaction can proceed without using any solvent, it is preferable to use a solvent selected from among ethers such as 1,4-dioxane, aromatic hydrocarbons such as benzene and toluene, aliphatic hydrocarbons such as hexane and heptane and mixtures thereof. When a solvent is to be used, it is preferable to employ a starting alcohol at a concentration of 1 to 50% by weight from the viewpoints of suppressing the formation of by-products and economically effecting the reaction.

Since the progress of the reaction might be inhibited by the presence of water in an amount exceeding 2 mol/l in the reaction mixture, the content of water should be adjusted to 2 mol/l or below.

(II) We have paid our attention to a fact that the yield of α-phenylpropionic acid derivative would widely vary depending on the solvent to be used and examined various solvents in order to further elevate the yield. As a result, we have found that the yield of α-phenylpropionic acid derivative can be unexpectedly elevated by using a mixture of a hydrocarbon and an oxygen-containing organic compound as a solvent when compared with the case wherein each component is used alone, thus completing the present invention.

The manner (II) of the present invention comprises using a mixture of a hydrocarbon and an oxygen-containing organic compound as a solvent. Any hydrocarbon may be used so long as it is present in liquid form under the reaction conditions. For example, aliphatic hydrocarbons such as pentane, hexane or cyclohexane, aromatic hydrocarbons such as benzene, toluene or xylene or mixtures thereof may be usually employed. Preferable examples of the oxygen-containing organic compound include organic carboxylic acids such as acetic, propionic and benzoic acids, ketones such as acetone and methyl ethyl ketone, ethers such as dioxane, tetrahydrofuran and diethyl ether and mixtures thereof.

The optimum ratio of the hydrocarbon to the oxygen-containing organic compound widely varies depending on the compounds to be used. For example, when hexane is used together with acetic acid, a ratio of acetic acid to hexane by volume of 2/98 to 30/70 would give preferable results.

It is preferable that the starting alcohol is contained in the abovementioned solvent mixture usually at a concentration of approximately 1 to 50% by weight.

The manner (II) of the present invention is carried out in the presence of a transition metal compound as a catalyst and, if required, a cocatalyst. Examples of the metal in the transition metal compound include rhodium, palladium, cobalt and nickel, while examples of the cocatalyst include halogen atoms and trivalent phosphorus compounds. Among these substances, it is particularly preferable in the present invention to use a rhodium compound as the transition metal compounds and iodine as the cocatalyst. More particularly, the rhodium compound may be selected from among rhodium halides, rhodium carbonyls and rhodium acetate and the iodine compound may be selected from among $I_2$, HI and alkyl iodides in general. When rhodium iodide is to be used as the rhodium compound, it is not always necessary to further add an iodine compound as a cocatalyst.

The reaction may be usually carried out at 30° to 130° C. A preferable reaction temperature ranges from 60° to 100° C. from the viewpoints of suppressing the formation of by-products and economically effecting the reaction.

The carbon monoxide and starting alcohol may be used in the same way as the one described in the manner (I).

(III) When an extremely expensive rhodium catalyst is to be used in the process of the present invention, it is necessary in practice to efficiently separate the rhodium catalyst from the product and to return the former to the reaction system to thereby reuse the same.

Distillation has been frequently used for separating and reusing a catalyst in such a homogeneous reaction system as the one described above. This method may be carried out in the following manner. Reaction product(s) and/or some portion of a reaction solvent are distilled off from a reaction mixture drawn from a reactor and the resulting distillation residue containing the catalyst is returned to the reactor as a catalyst. However it is disadvantageous to apply this method to the preparation of an α-phenylpropionic acid derivative with the use of a rhodium catalyst. This is because the product, which is an α-phenylpropionic acid derivative having a high boiling point, should be distilled under an extremely reduced pressure and at a high temperature, which would frequently result in the reduction of the rhodium catalyst to metallic rhodium and inactivation of the catalyst; and because a polymer of a styrene derivative, which is a by-product of the reaction, would gradually accumulate in the catalyst solution.

We have attempted to solve the above problems and consequently found that when an extraction solvent comprising water optionally with an oxygen-containing organic compound is added to a reaction mixture containing a rhodium catalyst and an α-phenylpropionic acid derivative, the reaction mixture is separated into a product-containing layer and an aqueous layer and most of the rhodium catalyst is extracted in the aqueous layer. Thus we have established a process for advantageously preparing an α-phenylpropionic acid derivative on an industrial scale by efficiently circulating a rhodium catalyst and have completed the present invention.

The rhodium catalyst may be used in the same manner as the one described above.

An iodine compound such as $I_2$, HI, an alkyl iodide or a metal iodide is added to the reaction system as a cocatalyst. In order to accelerate the carbonylation and to elevate the extraction yield, it is generally advantageous to add a large amount of the iodine compound to the reaction mixture. However the addition of the iodine compound would result in an increase in the formation of by-products. Thus the iodine compound is usually added in such an amount as to give a ratio of Rh to I on an atomic basis of approximately 1:0.5 to 1:6 to thereby give preferable results. When rhodium iodide or a rhodium catalyst recovered from the reaction mixture is to be used as a rhodium catalyst, it is not always necessary to further add an iodine compound.

In addition to those as cited above, carboxylic acids such as acetic acid and ketones such as acetone may be used as a reaction solvent.

After the reaction, water optionally together with an oxygen-containing organic compound is added to the reaction mixture to thereby extract the rhodium catalyst.

Common examples of the oxygen-containing organic compound include carboxylic acids such as acetic and propionic acids, ethers such as 1,4-dioxane and diethyl ether and ketones such as acetone and methyl ethyl ketone.

It should be determined depending on the composition of the reaction solvent whether water is used alone as an extraction solvent or a mixture of water and an oxygen-containing organic compound is employed therefor. Generally speaking, the addition of an oxygen-containing compound would elevate the extraction ratio of the rhodium, when the main component of the reaction solvent is a hydrocarbon such as hexane or benzene.

The optimum amount of the extraction solvent based on the amount of the reaction mixture varies depending on the combination of the solvents. When hexane is used as a reaction solvent and a mixture of water and acetic acid is used as an extraction solvent, preferable results may be obtained by using 0.1 to 1.0 part by volume of water and 0.1 to 2.0 parts by volume of acetic acid per part by volume of the reaction mixture.

The addition of the extraction solvent to the reaction mixture and the procedure from the separation of layers to the recovery of each layer should be carried out in a strictly controlled inactive gas atmosphere, preferably in a carbon monoxide atmosphere, to thereby inhibit the precipitation of the rhodium catalyst. After the completion of the reaction, some portion of the rhodium catalyst may sometimes solidify depending on, for example, the reaction solvent and reaction conditions. In this case, the solidified rhodium catalyst can be homogenized and extracted in the aqueous layer by heating the reaction mixture to 60° to 100° C. in a carbon monoxide atmosphere after the addition of the extraction solvent.

EXAMPLE

To further illustrate the present invention, and not by way of limitation, the following Examples will be given.

EXAMPLE 1

A 300-ml autoclave made of Hastelloy was changed with 9.0 g (50.6 mmol) of α-(4-isobutylphenyl)ethyl alcohol, 1.5 g (3.10 mmol) of rhodium iodide and 100 ml of dioxane, as a solvent, to cause a reaction to occur therein under a hydrogen pressure of 1 atm and a carbon monoxide pressure of 6 kg/cm$^2$ at 85° C. for three hours with stirring.

After cooling, the contents were taken out and the solvent was distilled off in vacuo. The residue was dissolved in 50 ml of benzene and 100 ml of a 2N aqueous solution of NaOH was added thereto to thereby extract the acidic component into the aqueous layer. Hydrochloric acid was added to the extract and an acid thus liberated was extracted with ether. After distilling off the ether, the obtained crude crystals were recrystallized from n-hexane to give 4.4 g of white crystals of α-(4-isobutylphenyl)propionic acid. The infrared and NMR spectra of this product were the same as those of a specimen.

EXAMPLE 2

A 300-ml autoclave made of Hastelloy C was charged with 9.3 g (76.2 mmol) of α-phenylethyl alcohol, 1.5 g (3.10 mmol) of rhodium iodide and 100 ml of dioxane, as a solvent, to cause a reaction to occur therein under the same conditions as those defined in Example 1. Thus 6.8 g of an oily mixture of α-phenylpropionic acid and β-phenylpropionic acid was obtained. As a result of liquid chromatography, it was found that this product comprised 86% by weight of α-phenylpropionic acid and 14% by weight of β-phenylpropionic acid.

EXAMPLE 3

A 300-ml autoclave made of Hastelloy C was charged with 1.5 g (3.10 mmol) of rhodium iodide and 100 ml of dioxane, as a solvent, to cause a reaction to occur therein under a hydrogen pressure of 10 kg/cm$^2$ and a carbon monoxide pressure of 30 kg/cm$^2$ at 150° C. with stirring. After cooling the reaction mixture and relieving the pressure, 8.9 g (50.0 mmol) of α-(4-isobutylphenyl)ethyl alcohol and 0.40 g (3.15 mmol) of iodine were further added thereto and then the procedure of Example 1 was repeated. Thus 4.5 g of α-(4-isobutylphenyl)propionic acid was obtained.

COMPARATIVE EXAMPLE 1

A 300-ml autoclave made of Hastelloy C was charged with 17.8 g (100 mmol) of α-(4-isobutylphenyl)ethyl alcohol, 2.7 g (150 mmol) of water, 193 mg (0.5 mmol) of [Rh(CO)$_2$Cl]$_2$, 52.4 mg (0.2 mmol) of triphenylphosphine and 17.8 ml of benzene, as a solvent, to cause a reaction to occur therein under a carbon monoxide pressure of 60 kg/cm$^2$ at 80° C. for five hours with stirring. After cooling, the contents were taken out and the solvent was distilled off in vacuo. The infrared spectrum of the obtained product showed no absorption around 1700 cm$^{-1}$, which is characteristic of carboxylic acids. Thus it was proved that no α-(4-isobutylphenyl)propionic acid was formed.

COMPARATIVE EXAMPLE 2

A 300-ml autoclave made of Hastelloy C was charged with 9.9 g (55.7 mmol) of α-(4-isobutylphenyl)ethyl alcohol, 0.205 g (0.780 mmol) of RhCl$_3$.3(H$_2$O), 25.5 g of a 57% aqueous solution of hydriodic acid and 100 ml of benzene, as a solvent, to cause a reaction to occur therein under a carbon monoxide pressure of 30 kg/cm$^2$ at 180° C. for two hours with stirring. After cooling, the contents were taken out and the solvent was distilled off in vacuo. The infrared and NMR spectra of the product and the result of gas chromatography thereof indicated that no carboxylic acid was formed and the whole α-(4-isobutylphenyl)ethyl alcohol was converted into polymers.

COMPARATIVE EXAMPLE 3

Reaction at too high a temperature

A 300-ml autoclave made of Hastelloy was charged with 9.2 g (51.7 mmol) of α-(4-isobutylphenyl)ethyl alcohol, 1.5 g (3.10 mmol) of rhodium iodide and 100 ml of dioxane, as a solvent, to cause a reaction to occur therein under the same conditions as those defined in Example 1 except that the reaction temperature was 180° C. After the completion of the reaction, the analysis of the contents indicated that 0.5 g of α-(4-isobutylphenyl)propionic acid was formed and the whole residue comprised an isobutylstyrene polymer and isobutylethylbenzene.

COMPARATIVE EXAMPLE 4

Reaction in the presence of excessive iodine

A 300-ml autoclave made of Hastelloy was charged with 9.0 g (50.6 mmol) of α-(4-isobutylphenyl)ethyl alcohol, 1.5 g (3.10 mmol) of rhodium iodide, 5.0 g (39.4 mmol) of iodine (Rh:I=1:12.7) and 100 ml of dioxane, as a solvent, to cause a reaction to occur therein under the same conditions as those defined in Example 1. After the completion of the reaction, the analysis of the contents indicated that 1.1 g of α-(4-isobutylphenyl)propionic acid was formed and the whole residue comprised an isobutylstyrene polymer.

COMPARATIVE EXAMPLE 5

Reaction in the presence of excessive water

A 300-ml autoclave made of Hastelloy was charged with 9.1 g (51.1 mmol) of α-(4-isobutylphenyl) ethyl alcohol, 1.5 g (3.10 mmol) of rhodium iodide, 5.8 g (322 mmol) of water, which gave a concentration of water in the reaction mixture of 2.9 mol/l, and 100 ml of dioxane, as a solvent, to cause a reaction to occur therein under the same conditions as those defined in Example 1. After the completion of the reaction, the gas chromatographic and NMR analysis of the contents indicated that 59% of the α-(4-isobutylphenyl) ethyl alcohol remained unreacted while 40% thereof was converted into 4-isobutylstyrene and α-(4-isobutylphenyl)propionic acid was formed only in a trace amount.

EXAMPLE 4

A 300-ml autoclave made of Hastelloy was charged with 9.8 g (55.1 mmol) of α-(4-isobutylphenyl) ethyl alcohol, 1.5 g (3.10 mmol) of rhodium iodide, and 5 ml of acetic acid and 95 ml of hexane, both as a solvent, to cause a reaction to occur therein under a hydrogen pressure of 1 atm and a carbon monoxide pressure of 6 kg/cm$^2$ at 85° C. for three hours with stirring. After cooling, the contents were taken out and the solvent was distilled off in vacuo. The residue was dissolved in 50 ml of benzene and 100 ml of a 2N aqueous solution of NaOH was added thereto to thereby extract the acidic component into an aqueous layer. Hydrochloric acid was added to the extract and an acid thus liberated was extracted with ether. After distilling off the ether, the obtained crude crystals were recrystallized from n-hexane. Thus 6.9 g (33.5 mmol) of white crystals of α-(4-isobutylphenyl) propionic acid were obtained (yield: 60.8%).

EXAMPLES 5 and 6

The procedure of Example 4 was repeated with the use of the solvents, starting alcohols and catalysts as shown in Table 1 under the conditions as defined therein. Table 1 shows the results.

TABLE 1

| | Ex. 5 | Ex. 6 |
|---|---|---|
| Solvent (ml/ml) | dioxane/hexane (20/80) | acetone/hexane (5/95) |
| Starting alcohol g (mmol) | α-(4-isobutylphenyl)-ethyl alcohol 9.8 (55.1) | α-(4-isobutylphenyl)-ethyl alcohol 9.6 (53.9) |
| Catalyst g (mmol) | RhI$_3$ 1.5 (3.1) | RhI$_3$ 1.5 (3.1) |
| Reaction temp. (°C.) | 85 | 85 |
| H$_2$/CO press. (atm/Kg/cm$^2$) | 1/6 | 1/6 |
| Product | α-(4-isobutylphenyl)-propionic acid | α-(4-isobutylphenyl)-propionic acid |
| Yield (% by mol) | 61.5 | 58.5 |

The following Examples will describe the separation, recovery and reuse of a rhodium catalyst in detail. Although these procedures were carried out batchwise, it is needless to say that a continuous reaction and continuous extraction by applying known techniques may be effected.

EXAMPLE 7

A 300-ml autoclave made of Hastelloy was charged with 9.8 g α-(4-isobutylphenyl) ethyl alcohol, 0.806 g (3.06 mmol) of rhodium chloride (RhCl$_3$.3H$_2$O), 1.20 g of iodine (I$_2$:9.47 mmol as I atom), and 100 ml of hexane and 5 ml of acetic acid, both as a solvent, to cause a reaction to occur therein under a hydrogen pressure of 1 atm and a carbon monoxide pressure of 10 kg/cm$^2$ at 85° C. for five hours with stirring.

After cooling, 60 ml of acetic acid and 30 ml of water were added to the reaction mixture in a carbon monoxide atmosphere and the resulting mixture was stirred for several hours and allowed to stand. Thus the reaction mixture was separated into two layers. The rhodium and reaction product in each layer were analyzed by atomic absorption spectroscopy and liquid chromatography respectively. Table 2 shows the results.

TABLE 2

|  | Weight (g) | Rhodium content (mg) | α-(4-isobutylphenyl)-propionic acid content (g) |
|---|---|---|---|
| Upper layer | 76.7 | 3.2 | 6.9 |
| Lower layer | 95.1 | 310 | 1.0 |

Table 2 suggests that 99.0% of the rhodium was extracted in the lower layer while 87.3% of the α-(4-isobutylphenyl) propionic acid was extracted in the upper layer.

After separating the lower layer, the solvent was distilled off therefrom in vacuo. Then the residue was reused in a reaction system to which α-(4-isobutylphenyl) ethyl alcohol, hexane and acetic acid were added according to the reaction conditions as defined above. As a result, a catalytic activity comparable to that of the first reaction was achieved.

EXAMPLE 8

The procedure of Example 7 was repeated except that 60 ml of 1,4-dioxane and 30 ml of water were employed as the extraction solvent. Table 3 shows the results.

TABLE 3

|  | Weight (g) | Rhodium content (mg) | α-(4-isobutylphenyl)-propionic acid content (g) |
|---|---|---|---|
| Upper layer | 94.8 | 0.76 | 6.7 |
| Lower layer | 69.6 | 310 | 0.5 |

EXAMPLE 9

The procedure of Example 7 was repeated except that 70 ml of water alone was used as the extraction solvent. Table 4 shows the results.

TABLE 4

|  | Weight (g) | Rhodium content (mg) | α-(4-isobutylphenyl)-propionic acid content (g) |
|---|---|---|---|
| Upper layer | 69.0 | 173 | 7.5 |
| Lower layer | 74.4 | 138 | 0.0 |

Although the extraction ratio of rhodium in this Example was as low as 44%, 100% of the product was extracted in the upper layer. Thus the rhodium can be readily separated from the product by further adding water to the recovered upper layer and repeating the extraction.

What is claimed is:

1. A process for preparing a compound having the formula (I)

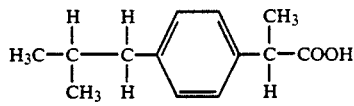

which comprises contacting at a temperature of from 60° to 100° C. (1) a compound having the formula (II)

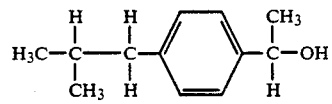

with (2) carbon monoxide, in the presence of a catalytically effective amount of (3) a rhodium halide-containing catalyst system effective to carbonylate the formula (II) compound and convert it to the formula (I) compound, the contacting being carried out in the presence of hexane and an oxygen-containing organic solvent selected from the group consisting of dioxane, acetone and acetic acid, said hexane and oxygen-containing solvent being present in said mixture in a volume ratio of from 95/5 to 80/20 of hexane to oxygen-containing organic solvent.

2. The process of claim 1, wherein said contacting is at a temperature of about 85° C.

3. The process of claim 1, wherein said rhodium halide is selected from the group consisting of rhodium iodide and rhodium chloride.

4. The process of claim 1, wherein said catalyst system also contains a material selected from the group consisting of $I_2$, HI and alkyl iodides.

5. The process of claim 1, wherein said oxygen-containing organic solvent is dioxane.

6. The process of claim 1, wherein said oxygen-containing organic solvent is acetone.

7. The process of claim 1, wherein said oxygen-containing organic solvent is acetic acid.

* * * * *